US012332178B1

(12) United States Patent
Jue et al.

(10) Patent No.: US 12,332,178 B1
(45) Date of Patent: Jun. 17, 2025

(54) METHOD AND APPARATUS FOR RAMAN SIGNAL ANALYSIS

(71) Applicant: Apollon Inc., Cheongju-si (KR)

(72) Inventors: Miyeon Jue, Seoul (KR); Young Kyu Kim, Seoul (KR); Aram Hong, Seoul (KR)

(73) Assignee: Apollon Inc., Cheongju-si (KR)

( * ) Notice: Subject to any disclaimer, the term of this patent is extended or adjusted under 35 U.S.C. 154(b) by 0 days.

(21) Appl. No.: 18/930,946

(22) Filed: Oct. 29, 2024

(30) Foreign Application Priority Data

Dec. 7, 2023 (KR) .................. 10-2023-0176634

(51) Int. Cl.
| | | |
|---|---|---|
| *G01N 21/65* | (2006.01) | |
| *G01J 3/02* | (2006.01) | |
| *G01J 3/12* | (2006.01) | |
| *G01J 3/44* | (2006.01) | |
| *A61B 5/145* | (2006.01) | |

(52) U.S. Cl.
CPC ............ *G01N 21/65* (2013.01); *G01J 3/0208* (2013.01); *G01J 3/0297* (2013.01); *G01J 3/12* (2013.01); *G01J 3/4412* (2013.01); *A61B 5/14532* (2013.01); *G01J 2003/1213* (2013.01)

(58) Field of Classification Search
CPC ....... G01N 21/65; G01N 33/49; G01J 3/0297; G01J 3/44; A61B 5/14532
See application file for complete search history.

(56) References Cited

U.S. PATENT DOCUMENTS

2018/0020956 A1* 1/2018 Lee ...................... A61B 5/0002
600/306

FOREIGN PATENT DOCUMENTS

| KR | 10-2015-0046132 A | 4/2015 | |
|---|---|---|---|
| KR | 10-2017-0057672 A | 5/2017 | |
| KR | 10-2018-0061959 A | 6/2018 | |
| KR | 10-2020-0018177 A | 2/2020 | |
| WO | WO-2022032218 A1 * | 2/2022 | ........... A61B 5/0075 |

* cited by examiner

*Primary Examiner* — Maurice C Smith
(74) *Attorney, Agent, or Firm* — United One Law Group LLC; Kongsik Kim; Jhongwoo Peck

(57) ABSTRACT

A Raman signal analysis device, which enables miniaturization of the device and non-invasive continuous monitoring of blood glucose level, includes a housing that forms an internal accommodation space therein; one or more light source units that are disposed within the housing and irradiate light onto a subject; a light receiving unit that obtains a Raman signal of light reflected or scattered from the subject using an optical filter array and an optical detection component array; and a processor configured to analyze biological information of the subject based on the Raman signal acquired by the light receiving unit.

9 Claims, 9 Drawing Sheets

METHOD AND APPARATUS FOR RAMAN SIGNAL ANALYSIS

CROSS-REFERENCE TO RELATED APPLICATION(S)

This application claims priority from Korean Application No. 10-2023-0176634 filed Dec. 7, 2023, which is incorporated herein by reference in its entirety.

TECHNICAL FIELD

The present disclosure relates to a Raman signal analysis technique, and more particularly, to methods and apparatuses for analyzing Raman signals using a plurality of light sources, filters, and detectors.

RELATED ART

The content described below merely provides background information related to the present disclosure and does not constitute prior art.

A continuous blood glucose monitoring device is a medical device that has a sensor attached to a patient (or a non-patient person) for an extended period of time to measure the patient's blood sugar level over a given period of time, check the increase and decrease trends in blood sugar level, and provide information so that the patient can control their diet or decide when to inject medicinal preparations such as insulin.

For this reason, in order to provide more appropriate health care for diabetic patients, domestic and international diabetes and endocrine societies have revised their guidelines and are recommending the use of continuous blood glucose monitoring devices regardless of the type of diabetes.

Most continuous glucose monitoring devices that are currently available commercially and approved by the U.S. Food and Drug Administration (FDA) for medical purposes use a method in which a needle of a metering device is inserted into the patient's body, and the blood sugar level measured from the needle is read using another device such as a smartphone.

Existing continuous blood glucose monitoring devices, which measure blood glucose invasively using needles, are painful to attach and can cause side effects such as inflammatory reactions due to their invasive nature. Additionally, these devices cannot be used for extended periods exceeding, typically, 15 days. Therefore, to address these issues, there is a need for technologies that can measure blood glucose level non-invasively.

Furthermore, a method to obtain various biometric information other than blood sugar in a noninvasive manner is needed.

SUMMARY

An aspect of the present disclosure is to provide a method for accurately analyzing biometric information using light sources of various wavelengths.

In addition, another aspect of the present disclosure is to provide a method for obtaining light of various wavelengths by distinguishing them using a plurality of optical filters and detectors.

The aspects of the present disclosure are not limited to those mentioned above, and other aspects will be clearly understood by those skilled in the art from the description below.

A Raman signal analysis device according to an exemplary embodiment of the present disclosure may include a housing that forms an internal accommodation space therein; one or more light source units that are disposed within the housing and irradiate light onto a subject; a light receiving unit that obtains a Raman signal of light reflected or scattered from the subject using an optical filter array and a light detection component array; and a processor configured to analyze biological information of the subject based on the Raman signal obtained by the light receiving unit.

Each of the one or more light source units may include a light source that outputs light of a wavelength band different from wavelength bands of other light sources in the one or more light source units; and a first lens, a first mirror, and a narrow-band optical filter disposed on a path along which the light output from the light source proceeds, and the light from the narrow-band optical filter may reach the subject through an aperture.

The light receiving unit may include a long pass filter disposed on a path of the light reflected or scattered from the subject; an optical filter array including an optical filter that corresponds to each light of the one or more light source units; a micro lens array that corresponds to the optical filter array; and an optical detection component array including an optical detection component that corresponds to each of the optical filters.

A Raman signal analysis device according to another exemplary embodiment of the present disclosure may include a housing that forms an internal accommodation space therein; a light source unit that is disposed within the housing and irradiates light onto a subject; a light receiving unit that obtains a Raman signal of light reflected or scattered from the subject; and a processor configured to analyze biological information of the subject based on the Raman signal obtained by the light receiving unit. The light receiving unit may include a beam splitter disposed on a path of the irradiated light and a light detection component, each of which receives the light split by the beam splitter.

The processor may be configured to extract biological information of the subject based on a peak area value of a Raman spectrum range corresponding to at least one of glucose, protein, ketone, alcohol, caffeine, lactic acid, or fat.

The processor may be configured to perform calibration by controlling the light source unit(s) and the light receiving unit in response to the Raman signal analysis device starting operation or being worn on the user's body.

The processor may be configured, when the calibration is performed, to control the light source unit(s) to output the light at a predetermined intensity during a predetermined time period, and set a light amount and an exposure time for the light source unit(s) for measuring blood sugar based on a peak corresponding to a specific Raman transition value among the Raman spectrum acquired during the predetermined time period by the light receiving unit.

A Raman signal analysis method according to an exemplary embodiment of the present disclosure may include outputting, by one or more light source units disposed in a housing that forms an internal accommodation space, light of different wavelengths onto a subject; obtaining, by a light receiving unit including an optical filter array and a light detection component array, a Raman signal of light reflected or scattered from the subject; and analyzing, by the processor, biological information of the subject based on the Raman signal obtained by the light receiving unit.

Each of the one or more light source units may output light of a different wavelength and include a light source, a lens, a mirror, and a narrow-band optical filter disposed on a path along which the light output from the light source proceeds, and the light from the narrow-band optical filter may reach the subject through an aperture.

The light receiving unit may include a long pass filter disposed on a path of the light reflected or scattered from the subject; an optical filter array including an optical filter that corresponds to each light of the one or more light source units, a micro lens array that corresponds to the optical filter array; and an optical detection component array including an optical detection component that corresponds to each of the optical filters.

Further, a computer program stored in a non-transitory computer-readable recording medium may be provided to execute a method disclosed in the present disclosure.

Further, a non-transitory computer-readable recording medium that contains program instructions, which when executed cause a processor to perform a method disclosed in the present disclosure may be provided.

According to the present disclosure, a method of analyzing Raman signals using a plurality of light sources, filters, and detectors is provided, whereby the bio-information of a subject can be acquired more accurately and effectively.

The effects of the present disclosure are not limited to those mentioned above, and other effects will be clearly understood by those skilled in the art from the description below.

DETAILED DESCRIPTION

Figure 1:
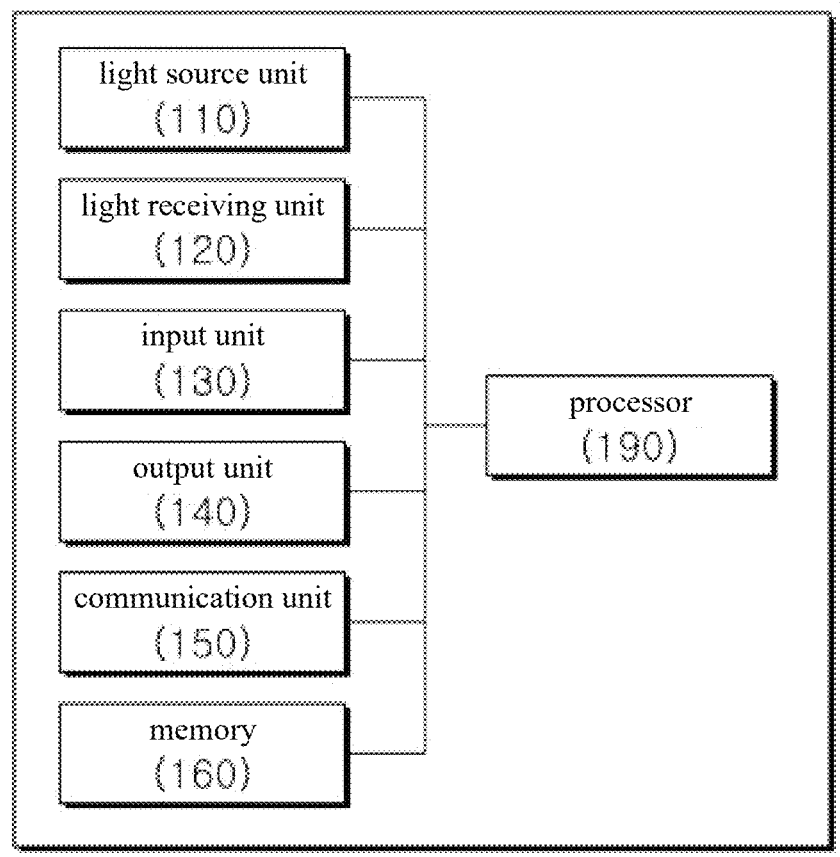
FIG. 1 is a block diagram illustrating the configuration of a Raman signal analysis device according to the present disclosure.

Throughout this disclosure, the same reference numerals denote the same components. The present disclosure may not describe all elements of the embodiments, and any content that is general in the technical field to which this disclosure belongs or that overlaps between embodiments may be omitted. The terms "unit," "module," "component," and "block" used in the specification can be implemented in software or hardware. Depending on the embodiments, a plurality of "units," "modules," "components," and "blocks" may be implemented as a single component, or a single "unit," "module," "component," and "block" may include a plurality of components.

Throughout the specification, when a part is said to be "connected" to another part, this includes not only cases where it is directly connected, but also cases where it is indirectly connected. The indirect connection may include a connection via a wireless communications network.

Also, when it is said that a part "comprises" or "includes" a component, it does not exclude the presence of other components unless specifically stated otherwise.

Throughout the specification, when an element is described as being disposed "on" another element, this includes not only the cases where the element is in contact with another element, but also the cases where one or more other elements exist between the two elements.

The terms "first," "second," and the like are used to merely distinguish one component from another and may not necessarily denote the order of components.

Singular expressions include plural expressions unless the context clearly indicates otherwise.

The reference numerals in each step are used for convenience of explanation and do not specify the order of the steps. Each step may be performed in a different order unless the context clearly indicates a specific sequence.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

The operating principle and embodiments of the present disclosure are described below with reference to the attached drawings.

The Raman signal analysis device according to the present disclosure may be implemented in various forms, including a wristwatch, wrist band, ring, belt, necklace, ankle band, thigh band, arm band, head band, or the like. However, the present disclosure is not limited thereto, and the Raman signal analysis device according to the present disclosure may be implemented in any form that is suitable for attaching to the body.

FIG. 1 is a block diagram illustrating the configuration of a Raman signal analysis device 100 according to the present disclosure.

Referring to FIG. 1, the Raman signal analysis device 100 according to the present disclosure may include a light source unit 110, a light receiving unit 120, an input unit 130, an output unit 140, a communication unit 150, a memory 160, and a processor 190. However, the present disclosure is not limited thereto, and the Raman signal analysis device 100 according to the present disclosure may include more or fewer components than the above-described components. These components may be arranged inside a housing that forms an internal accommodation space therein. Hereinafter, each of the components will be described in detail.

The light source unit 110 may be configured to emit light so that light can reach a subject (e.g., skin of a user). To this end, the light source unit 110 may include at least one optical component from among a light source that outputs light, a lens that focuses the emitted light on one spot, an optical filter that filters out some wavelengths of the emitted light, a mirror that changes the direction in which the emitted light proceeds, and a beam splitter that reflects some portion of the light and transmits other portion of the light.

As described above, the light source unit 110 may include a light source and may include at least one optical component that changes at least one of the direction of propagation of the light, wavelength, polarization state, or light quantity until the light emitted from the light source reaches the subject.

Here, the light source unit 110 may be implemented as one or more light source units, and each light source unit 110 may output light of a different wavelength. The processor 190 may be configured to control each light source unit 110 to perform scheduling for light output. In other words, the processor 190 may be configured to schedule light of different wavelengths to obtain specific bioinformation (e.g., blood sugar, glycated hemoglobin, ketones, alcohol, caffeine, lactic acid, or the like) using the corresponding light source unit 110.

The light receiving unit 120 may receive light reflected or scattered from the subject, obtain a Raman signal for Raman signal analysis, and generate a Raman spectrum. To this end, the light receiving unit 120 may include at least one of a lens that focuses light reflected or scattered from the subject to one point, an optical filter that filters out some wavelengths of light, a mirror that changes the direction in which light proceeds, or a diffraction member that disperses light by wavelengths to generate a spectrum of the light.

As described above, the light receiving unit 120 may include at least one configuration that changes at least one of the direction of propagation of the light, wavelength, polarization state, or light amount to generate a Raman spectrum by receiving light reflected or scattered from the subject, or generates a spectrum by dispersing the light by wavelengths.

Here, the light receiving unit 120 may be physically implemented as a plurality, and in such a case, a beam splitter may be arranged on the light transmission path so that light may be received by each of the plurality of light receiving units 120. In some embodiments, the light receiving unit 120 may be implemented as a single unit. In some other embodiments, the light receiving unit 120 may include an optical filter array, which includes a plurality of optical filters to obtain light reflected or scattered from the subject in various wavelength components, a micro lens array corresponding to the optical filter array, and an optical detection component array including a photo detection component corresponding to each of the optical filters. In some implementations, the photo detection component may be a photo detector. In other words, rather than physically including a plurality of light receiving units 120, the light receiving unit 120 may be implemented effectively as a plurality thereof by using an optical filter array, a micro lens array, and an optical detection component array. In such embodiments, the device can be miniaturized compared to the case in which a plurality of photo detection components are provided separately.

The input unit 130 may receive information that is input from a user. When information is input through the input unit 130, the processor 190 may be configured to control the operation of the device to correspond to the input information. The input unit 130 may include a hardware physical key (for example, a button disposed on at least one of the front, rear, or side of the device, a dome switch, a jog wheel, a jog switch, or the like) and/or a software touch key. By way of an example, the touch key may be formed of a virtual key, a soft key, or a visual key displayed on a touch screen type display through software processing, or may be formed of a touch key placed on a part other than the touch screen. The virtual key or visual key may have various forms and be displayed on the touch screen, and may be formed of, for example, a graphic, a text, an icon, a video, or a combination thereof.

The output unit 140 may generate output associated with vision, hearing, or tactile sensations, and may include at least one of a display, an audio output device, a haptic module, or an optical output device.

The display may be implemented as a touch screen by forming a layered (e.g., laminated) structure or an integral structure with the touch sensor. The touch screen may function as a user input unit that provides an input interface between the device 100 and the user, and at the same time, may provide an output interface between the device and the user.

The audio output device may output audio data received through the communication unit or stored in the memory, or may output audio signals associated with functions performed by the device. The audio output device may include a receiver, a speaker, a buzzer, or the like.

The communication unit 150 may include one or more components that enable communication with an external device, and may include, for example, at least one of a wired communication module, a wireless communication module, or a short-range communication module.

The memory 160 may store data associated with various functions of the device 100 and a program for the operation of the processor 190. The memory 160 may store input/output data, application programs (or applications) that are run on the device 100, and data and commands for the operation of the device 100. At least some of these application programs may be downloadable from an external server via wireless communication. The memory 160 may be separately provided from the device. In some such embodiments, the memory 160 may include a database connected by wire or wirelessly.

The processor 190 may be implemented as a memory that stores data for an algorithm for controlling the operation of components within the device or a program to implement the algorithm, and at least one processor configured to perform the aforementioned operation based on the data stored in the memory. In some embodiments, the memory and the processor 190 may be implemented as separate chips. In some other embodiments, the memory and the processor 190 may be implemented as a single chip.

In addition, the processor 190 may be configured to control one or more of the components described above in combination, in order to implement on the device various embodiments according to the present disclosure to be described with reference to FIGS. 2-9 below.

Meanwhile, the function associated with artificial intelligence according to the present disclosure may be performed through a processor and a memory. The processor may be composed of one or more processors. As such, the one or more processors may be implemented as a general-purpose processor such as a CPU, an AP, a Digital Signal Processor (DSP), a graphics-only processor such as a GPU, a Vision Processing Unit (VPU), or an artificial intelligence-only processor such as an NPU. The one or more processors may be configured to control input data to be processed according to predefined operation rules or artificial intelligence models stored in the memory. Alternatively, when the one or more processors are implemented with artificial intelligence-only processors, they may be designed with a hardware structure specifically designed for processing a specific artificial intelligence model.

The predefined operation rules or artificial intelligence models may be created through learning. Here, being created through learning may mean that the basic artificial intelligence model learns by using a plurality of training data by a learning algorithm, thereby creating a predefined operation rules or artificial intelligence model configured to perform a desired characteristic (or purpose). Such learning may be performed in the device itself on which the artificial intelligence according to the present disclosure is performed, or may be performed through a separate server and/or system. Examples of the learning algorithm may include supervised learning, unsupervised learning, semi-supervised learning, or reinforcement learning. However, the present disclosure is not limited to the examples described above.

The artificial intelligence model may be composed of a plurality of neural network layers. The plurality of neural network layers may have a plurality of weight values, and may perform neural network operations through operations between the results of the previous layer and the plurality of weight values. The plurality of weight values of the plurality of neural network layers may be optimized by the learning results of the artificial intelligence model. For example, the plurality of weight values may be updated so that the loss value or cost value acquired from the artificial intelligence model is reduced or minimized during the learning process. The artificial neural network may include a deep neural network (DNN), and examples thereof include, but are not limited to, a convolutional neural network (CNN), a deep neural network (DNN), a recurrent neural network (RNN), a restricted boltzmann machine (RBM), a deep belief network (DBN), a bidirectional recurrent deep neural network (BRDNN), or deep Q-networks.

According to an exemplary embodiment of the present disclosure, a processor may be configured to implement artificial intelligence. Artificial intelligence refers to a machine learning method based on an artificial neural network that imitates human neurons (biological neurons) to enable a machine to learn. Artificial intelligence methodologies can be divided into supervised learning in which input data and output data are provided together as training data according to a learning method, so that an answer (output data) to a problem (input data) is determined, unsupervised learning in which only input data is provided without output data, so that an answer (output data) to a problem (input data) is not determined, and reinforcement learning in which learning is performed in a direction to maximize a reward, which is given from an external environment whenever an action is taken in a current state (State). In addition, artificial intelligence methodologies can be categorized by architecture, which represents the structure of the learning model. The architectures that are widely used in the deep learning technologies can be categorized into convolutional neural networks (CNNs), recurrent neural networks (RNNs), transformers, and generative adversarial networks (GANs).

The device may include an artificial intelligence model. The artificial intelligence model may be implemented as a single artificial intelligence model or may be implemented as a plurality of artificial intelligence models. Each of the one or more artificial intelligence models may be composed of a neural network (or an artificial neural network) and may include a statistical learning algorithm that mimics biological neurons in machine learning and cognitive science. A neural network may refer to a model in which artificial neurons (nodes) that form a network by combining synapses change the strength of the synapses through learning, thereby exhibiting a problem-solving ability. The neurons of the neural network may include a combination of weights or biases. The neural network may include one or more layers composed of one or more neurons or nodes. For example, the device may include an input layer, a hidden layer, and an output layer. The neural network constituting the device may infer a desired result (output) from an arbitrary input (input) by changing the weights of the neurons through learning.

Hereinbelow, various Raman signal analysis devices according to the present disclosure are described.

Figure 2:
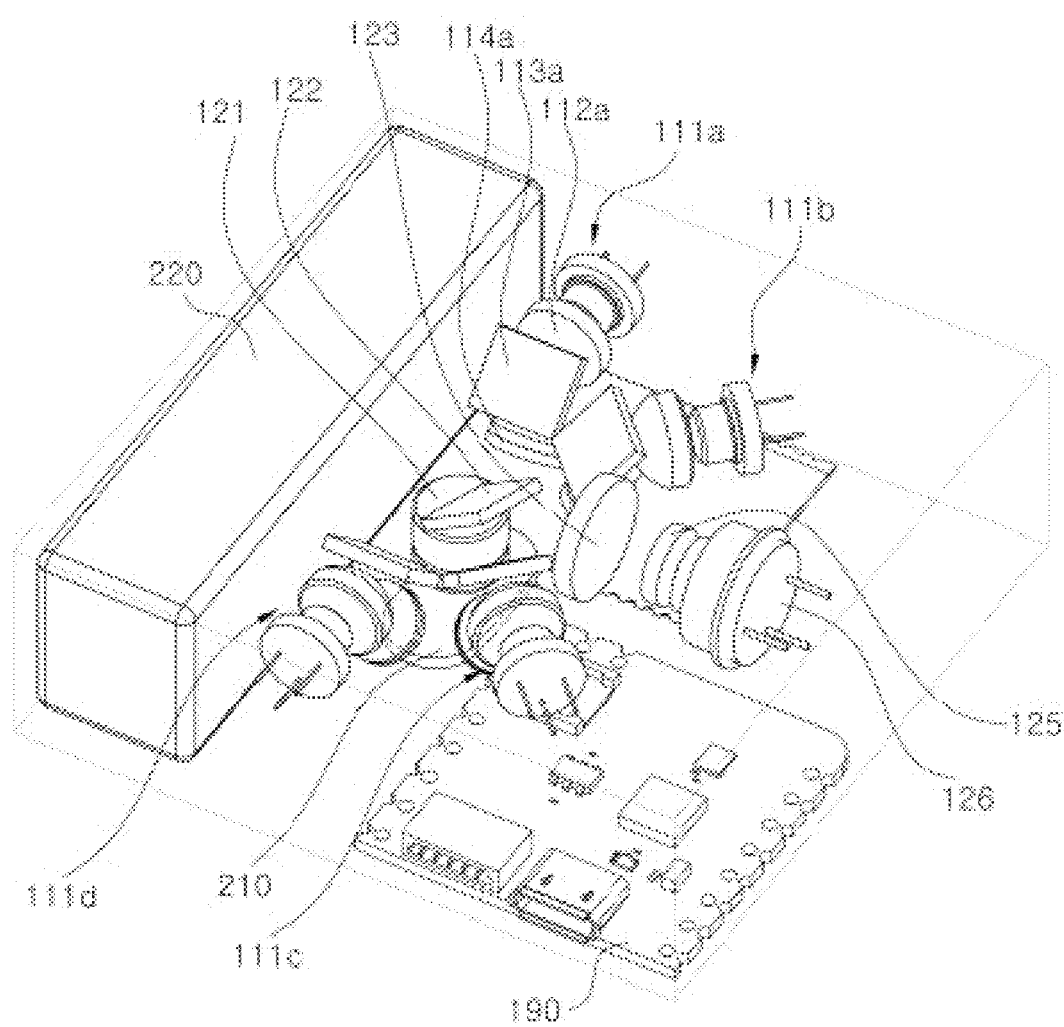
FIG. 2 is a perspective view illustrating the internal structure of a Raman signal analysis device including a plurality of light sources according to the present disclosure.
Figure 3:
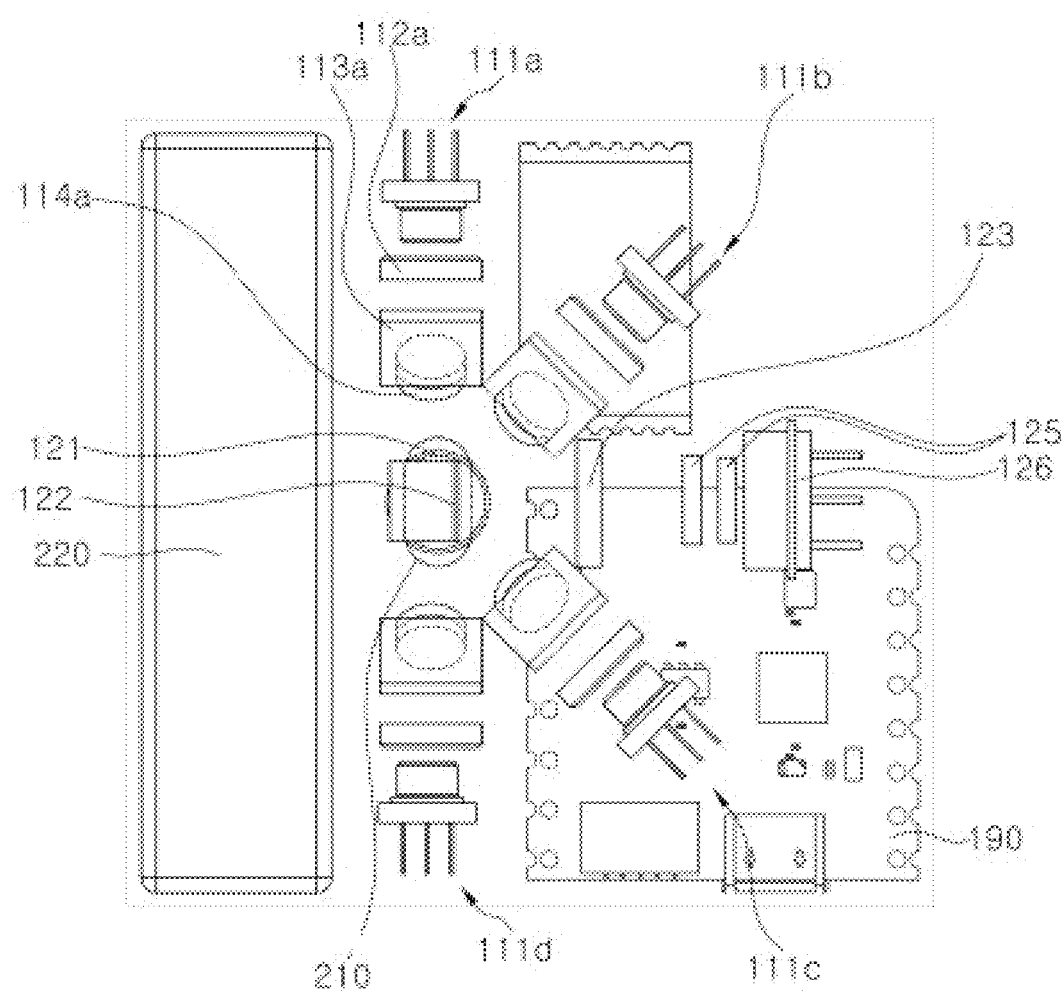
FIG. 3 is a plan view illustrating the internal structure of a Raman signal analysis device including a plurality of light sources according to the present disclosure.

FIG. 2 is a perspective view illustrating the internal structure of a Raman signal analysis device 100 including a plurality of light sources according to the present disclosure, and FIG. 3 is a plan view illustrating the internal structure of a Raman signal analysis device 100 including a plurality of light sources according to the present disclosure.

Referring to FIGS. 2 and 3, each component of the Raman signal analysis device 100 may be disposed inside a housing that forms an internal accommodation space. However, the embodiment is not limited thereto.

The light source unit 110 may be disposed within the housing and may irradiate light to the subject. The light source unit 110 may be implemented in a plurality of light source units. Each of the plurality of light source units may include a light source 111a-111d that outputs light of different wavelengths, a first lens (e.g., 112a), a first mirror (e.g., 113a), and a narrow-band optical filter (e.g., 114a) that are placed on the path of light output from the light sources 111-111d. The narrow-band optical filter 114a may be configured to increase wavelength specificity for the corresponding light source 111a.

Each light source 111a-111d of the light source unit 110 may irradiate light to the subject. For example, the light sources 111a-111d may irradiate near infrared rays (NIR) or mid infrared rays (MIR) to the subject. However, the wavelength emitted from the light sources 111a-111d may vary depending on the measurement purpose.

In some embodiments, the light sources 111a-111d may be implemented with light emitting diodes (LEDs) or laser diodes. However, the present disclosure is not limited thereto.

The light output from the light sources 111a-111d may pass through the first lens (e.g., 112a) and may be focused onto the first mirror (e.g., 113a). The first lens 112a may focus the light emitted from the light source 111a onto the first mirror 113a. Accordingly, the first lens 112a may minimize battery consumption by eliminating the need to increase the output of the light source 111a above a certain level.

The light that passes through the first lens 112a may be reflected by the first mirror 113a. The reflected light may pass through a narrow-band optical filter 114a. Herein, description is provided for a corresponding set of light source 111a, first lens 112, first mirror 113a, and narrow-band optical filter 114a, included in one of the light source units 110. However, the description may be applied for other light source units 110.

The light that passes through the narrowband optical filter 114a may be emitted to the exterior of the Raman signal analysis device 100 through an aperture 210. Here, the aperture 210 may be formed on one surface of the housing. For example, the housing may include a surface that may come into contact with the subject when the device 100 is worn on the subject, and the aperture 210 may be formed on the contact surface to allow light emitted from the light source to be emitted to the exterior of the Raman signal analysis device 100 and to allow light reflected or scattered from the subject to return to the interior of the Raman signal analysis device 100.

When the Raman signal analysis device 100 according to the present disclosure is mounted so that the contact surface is in contact with the body, the light emitted to the exterior may reach the subject (e.g., skin).

The light that reaches the subject may be reflected or scattered and may enter the aperture 210. The light that enters the aperture 210 may pass through a long pass filter 121 disposed on the light transmission path. The long pass filter 121 may block general reflected light and Rayleigh scattered light, which return from the subject, and may allow only the Raman scattering signal to pass through, thereby increasing the signal-to-noise ratio.

In some embodiments, the light that passes through the long wavelength pass filter 121 may be reflected by a second mirror 122. The light reflected by the second mirror 122 may be collected by a second lens 124. In some embodiments, a separate optical filter may be disposed between the second mirror 122 and the second lens 123. Further, the long wavelength pass filter 121, the second mirror 122, and the second lens 123 may be included in the light receiving unit 120.

The photodetector 120 may detect a Raman signal of a specific wavelength using a single detector (e.g., photodiode).

In some embodiments, in order to measure a 1125 $cm^{-1}$ Raman signal peak that is for measuring blood sugar with an 830 nm light source, the light receiving unit 120 may include a 915 nm wavelength band filter in front of the light detector such as an avalanche photodiode (APD), photodiode (PD), charge-coupled device (CCD), or complementary metal-oxide-semiconductor (CMOS).

In some embodiments, the light receiving unit 120 having a different wavelength band may obtain a Raman signal of 1815 $cm^{-1}$ by using a 785 nm light source, and a Raman signal of 840 $cm^{-1}$ by using 850 nm. Generally, information on the concentration of a specific biomaterial in the body can be more accurately determined by obtaining Raman signals in more various ranges.

The light receiving unit 120 may detect light of each wavelength band through an optical filter 125, or an optical filter array, and an optical detection component 126 (e.g., an optical detection unit, or an optical detection array).

In some embodiments, the light receiving unit 120 may include light sources and light filters of various wavelength bands to obtain Raman signals for various bioinformation (e.g., glucose, protein, ketone, alcohol, caffeine, lactic acid, and fat).

In some such embodiments, red light and/or near-infrared light with a wavelength of about 600 nm or more, which have relatively high light transmittance in the body, may be used as the light source for the ease of measuring substances in the body. After the wavelength band with the greatest influence is set by a combination of a single light source and a single filter, longer and/or shorter wavelengths within a preset range (e.g., 10 nm) compared to the basic light source wavelength may be additionally included. In addition, a light source wavelength may be selected for use for background signal removal and/or for calibration by measuring the Raman signal wavelength band of other biological substances (e.g., 1450 $cm^{-1}$ for proteins).

The Raman signal analysis device 100 according to the present disclosure may include a battery 220 for powering the above-described components. The battery 220 may be detachable or externally mounted to the housing. However, the present disclosure is not limited thereto.

The processor 190 may be configured to analyze the subject's bio-information based on the Raman signal acquired by the light receiving unit 120.

Figure 4:
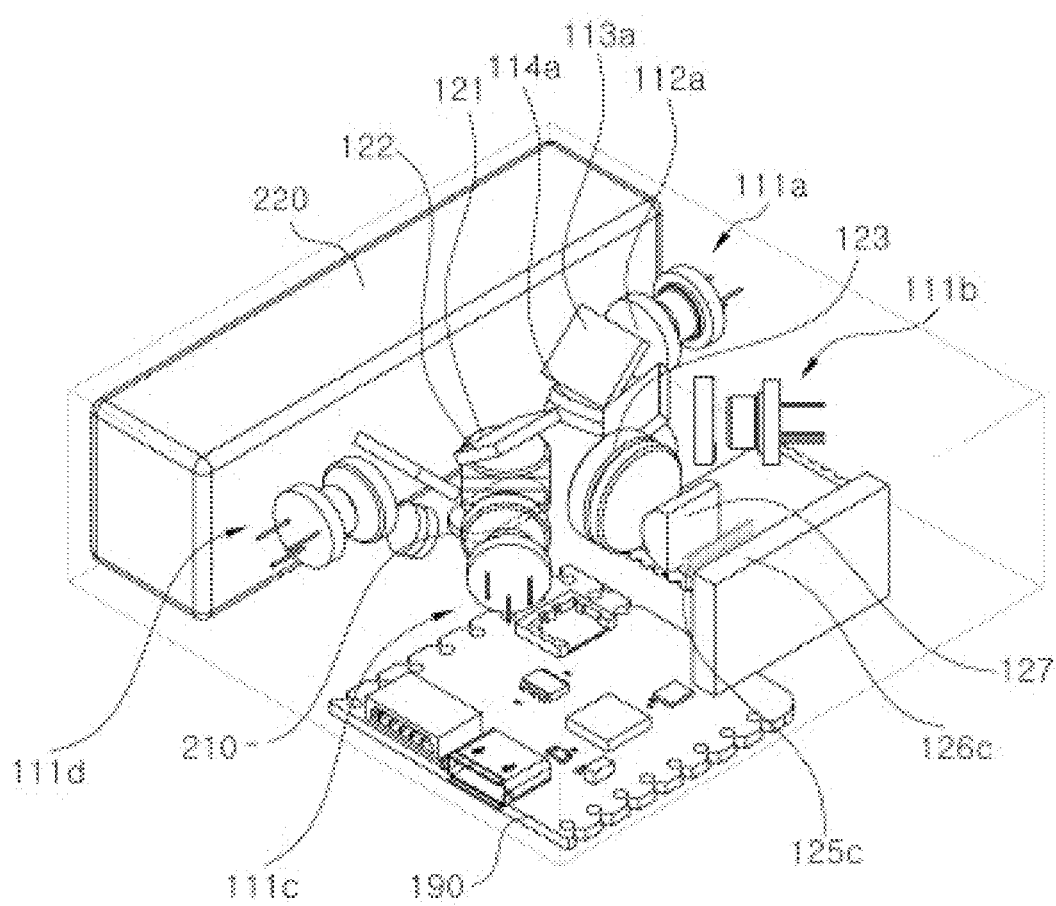
FIGS. 4 and 5 are perspective views illustrating the internal structure of a Raman signal analysis device including a plurality of light sources and a light detection component array according to the present disclosure.
Figure 5:
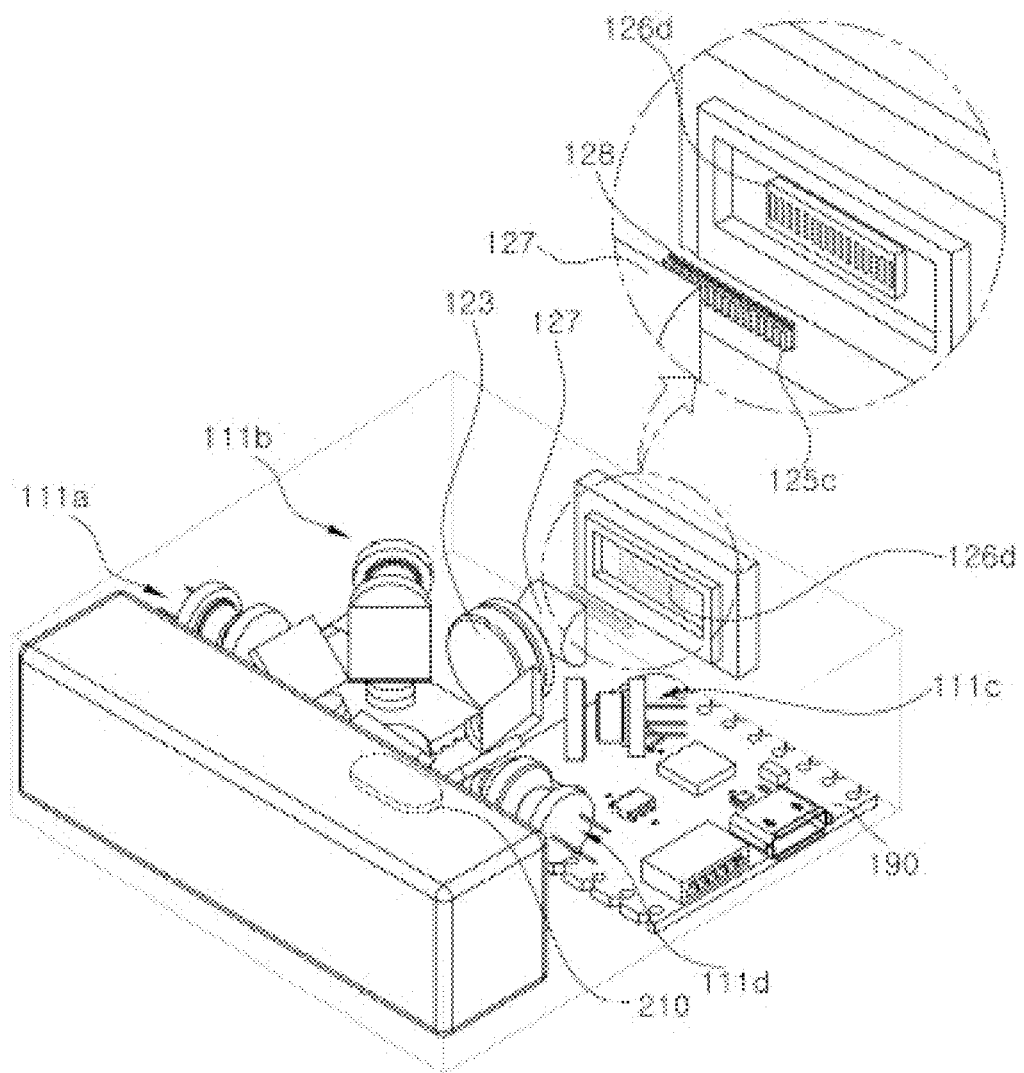
Figure 6:
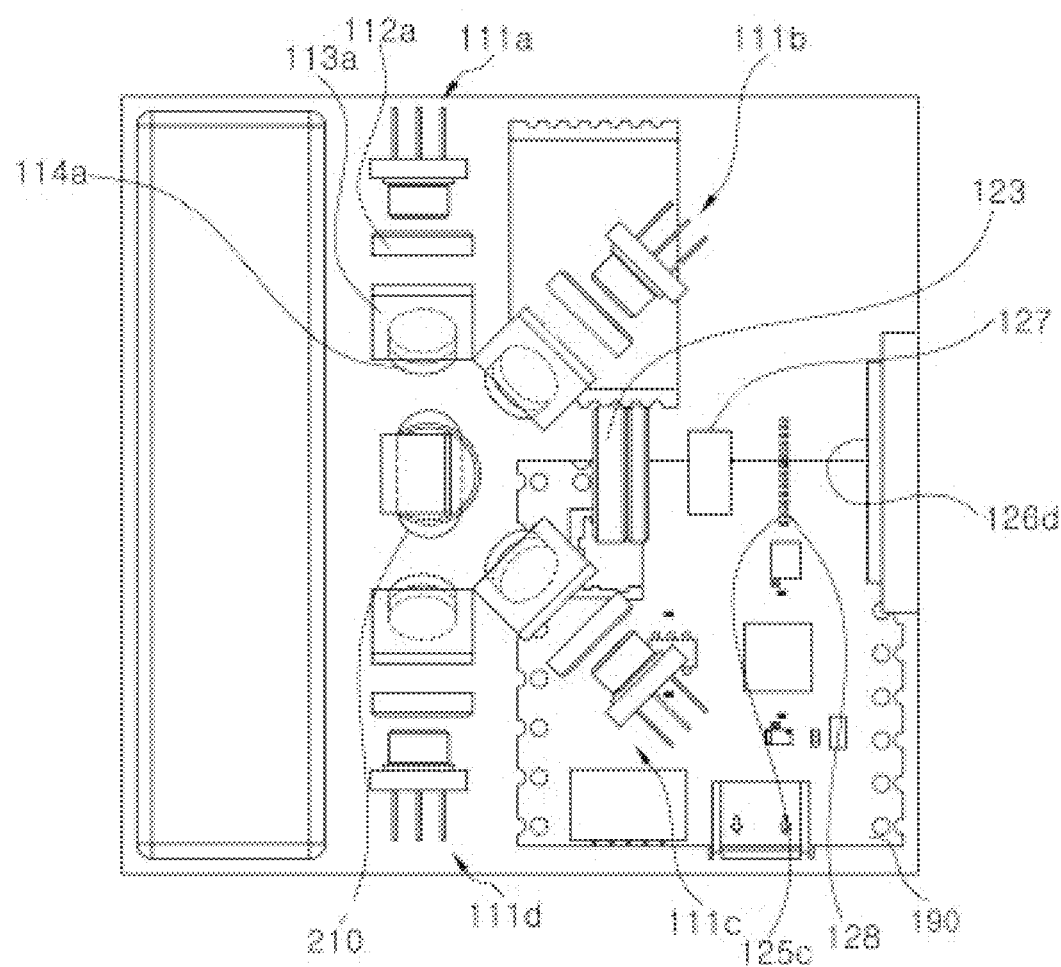
FIG. 6 is a plan view illustrating the internal structure of a Raman signal analysis device including a plurality of light sources and a light detection component array according to the present disclosure.

FIGS. 4 and 5 are perspective views illustrating the internal structure of a Raman signal analysis device including a plurality of light sources and an array of light detection components according to the present disclosure. FIG. 6 is a plan view illustrating the internal structure of a Raman signal analysis device including a plurality of light sources and an array of light detection components according to the present disclosure. The differences from the embodiment shown in FIGS. 2 and 3 will be mainly explained.

The plurality of light sources 111a-111d of FIGS. 4-6 may be substantially identical to the plurality of light sources 111a-111d illustrated in FIGS. 2 and 3, and the light receiving unit 120 of FIGS. 4-6 may include a long wavelength pass filter 121 and a second mirror 122 shown in FIGS. 2 and 3, and may optionally include a second lens 123.

The light receiving unit 120 may obtain a Raman signal of light reflected or scattered from a subject through a light filter array 125c and a light detection component array 126d for the plurality of light sources 111a-111d that output a plurality of different wavelength bands.

The light receiving unit 120 may include a cylinder lens 127 before the light filter array 125c on the light transmission path, and may include a micro lens array 128 after the light filter array 125c.

The cylinder lens 127 may collect light and provide the light to the optical filter array 125c, and the optical filter array 125c may include an optical filter corresponding to each light of the plurality of light sources 111a-111d. The micro lens array 128 may be implemented with a micro lens array that is aligned with the optical filter array 125c, may correspond to the optical filter array 125c, and may allow the filtered light to be received by each optical detection component of the small-sized optical detection component array 126d. The optical detection component array 126d may correspond to each optical filter.

Each optical filter of the optical filter array 125c may extract only the light of a preset wavelength range, and each optical detection component of the optical detection component array 126d may receive the light and convert it into an electrical signal representative of the amount of received light.

Due to the configuration of this exemplary embodiment, light of various wavelength bands colliding with various biological materials may be obtained without needing to include multiple light detectors and beam splitters, thereby enabling a more compact form factor for the device. In addition, this structure may allow various Raman signals to be obtained even though a single light source is used.

The processor 190 may be configured to enable generation of a Raman spectrum through an electrical signal. For example, each light detection component of the light detection component array 126d may be implemented as a Charge Coupled Device (CCD), an avalanche photodiode (APD) array, a photodiode (PD), and/or a complementary metal-oxide-semiconductor (CMOS), but the embodiment is not limited thereto.

The processor 190 may be configured to generate a Raman spectrum based on a signal generated from the light detection component array 126d. The Raman spectrum may be generated such that it may be represented by a graph in which the x-axis is the Raman shift value (unit: $cm^{-1}$) and the y-axis is the signal intensity.

The processor 190 may be configured to measure the biological information of the subject by analyzing the generated Raman spectrum, and may be configured to extract the biological information of the subject through the peak area value of the Raman spectrum range corresponding to at least one of glucose, protein, ketone, alcohol, caffeine, lactic acid, or fat of the subject.

For example, taking blood sugar as an example, the processor 190 may be configured to perform a calibration process for Raman spectra specific to the blood sugar and skin-forming protein prior to measuring the blood sugar of the subject.

In some embodiments, during the calibration, the processor 190 may be configured to reduce noise in the generated spectrum through Savitzky-Golay filtering and to remove the background of the generated spectrum through polynomial fitting. The order of the polynomial fitting that is suitable for background removal may be determined based on the intensities of four wavelengths: namely, the initial wavelength, the wavelength at the two-quarter point, the wavelength at the three-quarter point, and the end wavelength.

Re-calibration may be performed when the processor 190 of the device is started, blood glucose measurement is stopped and then restarted, or the device is temporarily removed and then re-worn.

In some embodiments, when the device starts operating or is re-worn, the processor 190 may be configured to control the light source unit to output light at a predetermined output for a predetermined period of time. Subsequently, based on a peak corresponding to a predetermined Raman transition value among the Raman spectrum acquired for the predetermined period of time by the light receiving unit, the processor 190 may be configured to set the light amount and exposure time of the light source unit to be used for measuring blood sugar.

Herein, the Raman signal intensity corresponding to the predetermined Raman transition value may be a peak at about 1450 $cm^{-1}$.

During the calibration, if the Raman signal intensity corresponding to the predetermined Raman transition value does not reach the reference value even with the maximum output and maximum exposure time of the light source unit, the processor 190 may be configured to control the communication unit so that an error message is transmitted to an external terminal.

A user may check the error message through the external terminal connected to the Raman signal analysis device 100 according to the present disclosure. The error message may include text or an image requesting a change of the attachment site or re-attachment of the device 100.

Meanwhile, if the intensity ratios of the acquired Raman signal picks differ from the intensity ratios of general Raman signal peaks by a predetermined threshold or more, the processor 190 may be configured to determine that there is poor contact between the subject and the device, and to control the communication unit 150 to transmit an error message to the external terminal.

However, without being limited thereto, the processor 190 may be configured to display an error message through the output unit 140 included in the continuous blood glucose measurement device 100, rather than transmitting the aforementioned error message to an external terminal.

Thereafter, the processor 190 may be configured to utilize machine learning techniques such as partial least squares (PLS), support vector machine (SVM), or deep learning using autoencoder, ResNet, or the like to correlate the peak area corresponding to each of glucose, protein, fat, ketone, alcohol, lactic acid, caffeine, or the like with the glucose level at the time of measurement. Accordingly, various bio-information including blood sugar of the subject may be continuously measured based on the learned model.

In some embodiments, the glucose level may be measured through a method such as finger prick, venous blood prick, continuous CGM, or the like. However, the method of measuring the glucose level is not limited thereto.

In some embodiments, the processor 190 may be configured to estimate the amount of glucose in the interstitial fluid based on the ratio of the area of the peak having a center value of about 1450 $cm^{-1}$ to the area of the peak having a center value of about 1660 $cm^{-1}$ and the area of the peak having a center value of about 1125 $cm^{-1}$.

Herein, for the peak with a center value of about 1450 $cm^{-1}$, which corresponds to protein, the area may be calculated using the range of 1415 $cm^{-1}$ to 1480 $cm^{-1}$.

Further, for the peak with a center value of about 1660 $cm^{-1}$, which corresponds to fat, the area may be calculated using the range of 1630 $cm^{-1}$ to 1685 $cm^{-1}$.

Further, for the peak with a center value of about 1125 $cm^{-1}$, which corresponds to glucose, the area may be calculated using the range of 1100 $cm^{-1}$ to 1145 $cm^{-1}$.

In some embodiments, the processor 190 may be configured to obtain an area corresponding to ketone by using a range of $1700^{-1}$ to 1750 $cm^{-1}$ for the peak with a center value of about 1725 $cm^{-1}$, which corresponds to ketone.

In some embodiments, the processor 190 may be configured to obtain an area corresponding to alcohol by using a range of 1180 $cm^{-1}$ to 1220 $cm^{-1}$ for the peak with a center value of about 1200 $cm^{-1}$, which corresponds to alcohol.

In some embodiments, the processor 190 may be configured to obtain an area corresponding to the carbon-oxygen double bond of caffeine (i.e., carbonyl group of a caffeine molecule) by using a range of 1600 $cm^{-1}$ to 1700 $cm^{-1}$ for the peak with a center value of about 1650 $cm^{-1}$.

In some embodiments, for lactic acid, the processor 190 may be configured to obtain an area corresponding to the carboxyl group by using a range of 1700 $cm^{-1}$ to 1750 $cm^{-1}$ for the peak with a center value of about 1725 $cm^{-1}$.

As described above, the Raman signal analysis device 100 according to the present disclosure may obtain bio-information non-invasively, resulting in significantly fewer side effects compared to existing devices that require needle injection.

In some embodiments, the aperture may be disposed substantially at the center. In the conventional design of a spectrometer for generating a Raman spectrum, an aperture is typically disposed at an outer corner rather than the center of the device to ensure a stable optical path for securing the light dispersion angle of a monochromator.

However, according to the present disclosure, the aperture may be disposed at or near the center of the main body. In the case of a wearable device to be attached to the body, the main body and the user's body may be separated due to the user's activity. Since the center of the main body of the wearable device is likely to make the strongest contact with the user's body, the distance between the light source and the subject may be stably maintained as the aperture is disposed at the center of the contact surface of the housing.

To this end, according to the present disclosure, the aperture may be disposed at the center of the contact surface included in the housing, and the light detection component and an internal battery 220 may be disposed at the outermost part inside the main body. The light source may be disposed so as to face the aperture disposed at the center of the contact surface. Accordingly, the angle formed between the path of light incident from the light source to the first mirror and the path of light incident to the optical filter array may become greater than 90 degrees.

As described above, according to the present disclosure, the accuracy of biometric information measurement may be improved by positioning the aperture through which the light irradiated to the subject is emitted at the center of the device.

Further, according to the present disclosure, the battery may be replaced without terminating or interrupting the continuous blood glucose measurement.

Figure 7:
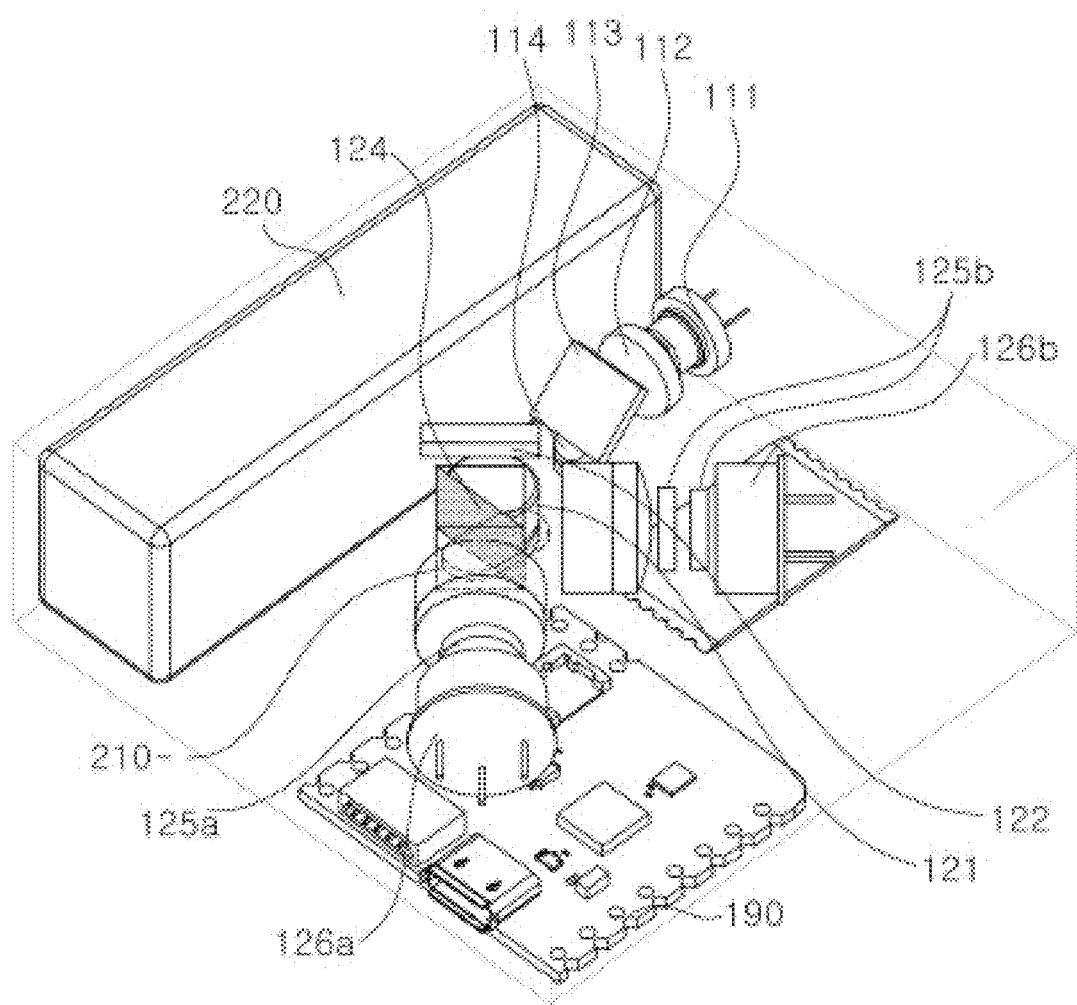
FIG. 7 is a perspective view illustrating the internal structure of a Raman signal analysis device including a plurality of light detection components according to the present disclosure.

FIG. 7 is a perspective view illustrating the internal structure of a Raman signal analysis device including a plurality of photodetector components according to the present disclosure.

The light source unit 110, as shown in FIG. 7, may be implemented as a single light source 111. The light receiving unit 120 may include a beam splitter 124 disposed on the path of the irradiated light, such that optical filters 125a and 125b and light detection components 126a and 126b that respectively receive the light split by the beam splitter 124 may obtain a Raman signal of light reflected or scattered from the subject.

In some embodiments, for measuring blood sugar with an 830 nm light source, the processor 190 may be configured to obtain a 1125 $cm^{-1}$ Raman signal by disposing a 915 nm wavelength band filter in front of a photodetector such as an APD, CMOS, CCD, or APD array to measure the 1125 $cm^{-1}$ Raman signal peak. Thereafter, by using a 930 nm filter in another photodetector, a 1295 $cm^{-1}$ Raman signal may be obtained. Further, by using a 900 nm filter, a 937 $cm^{-1}$ Raman signal may be obtained. As more areas of Raman signals are obtained, information on the in-vivo concentration of a specific biological substance may be determined more accurately.

The wavelength band in which the Raman signal of a specific biomaterial is most affected may be set as the basic filter wavelength by the combination of a single light source and a single filter. Subsequently, one or more wavelengths longer and/or shorter than the basic filter wavelength may be used by the combination of filters and light sources. In order to obtain more information regarding the wavelength band over which a specific biomaterial has the most significant influence, a filter within 10 nm from the basic filter wavelength may be added. Further, to remove the background signals and/or to calibrate, a wavelength filter may be selected based on the measurement in the wavelength band of the Raman signal of other biomaterials (e.g., protein, 1450 $cm^{-1}$).

Figure 8:
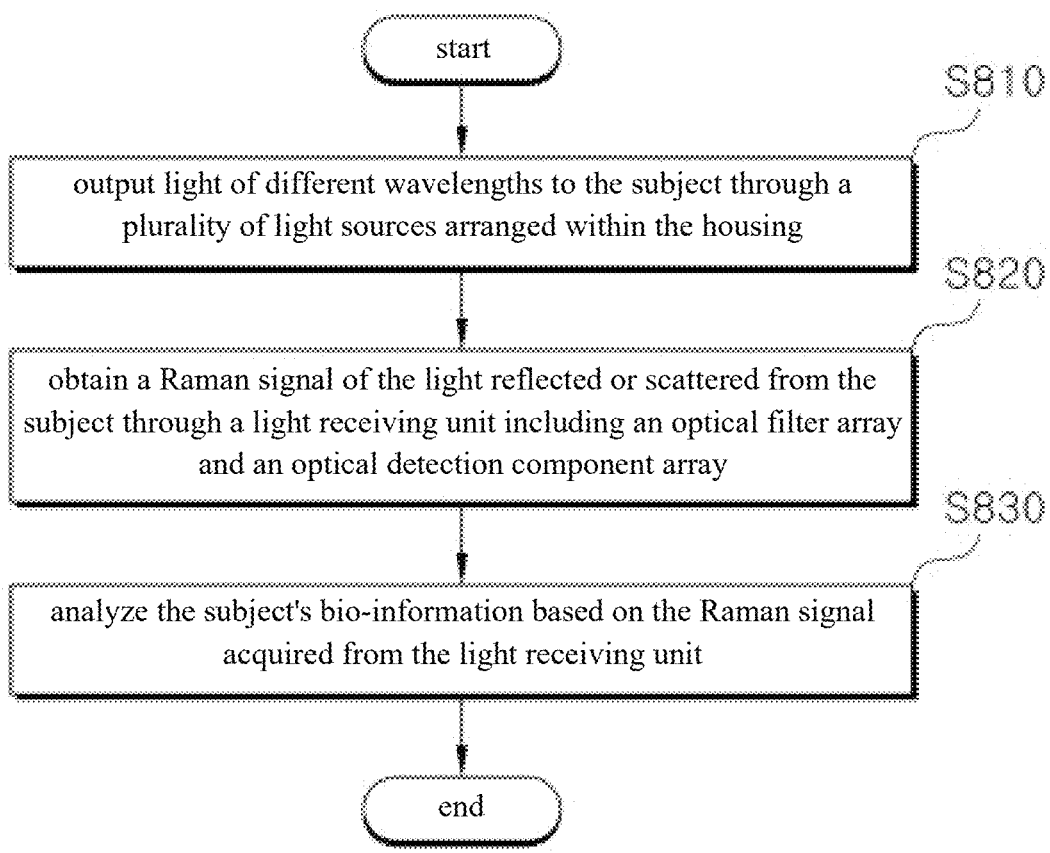
FIG. 8 is a flowchart describing an analysis method of a Raman signal analysis device including a plurality of light sources according to the present disclosure.

FIG. 8 is a flowchart describing an analysis method of a Raman signal analysis device including a plurality of light sources according to the present disclosure.

At step S810, the processor 190 may be configured to output light of different wavelengths to the subject through a plurality of light sources arranged within the housing.

At step S820, the processor 190 may be configured to obtain a Raman signal of the light reflected or scattered from the subject through a light receiving unit including an optical filter array and an optical detection component array.

At step S830, the processor 190 may be configured to analyze the subject's bio-information based on the Raman signal acquired from the light receiving unit.

Figure 9:
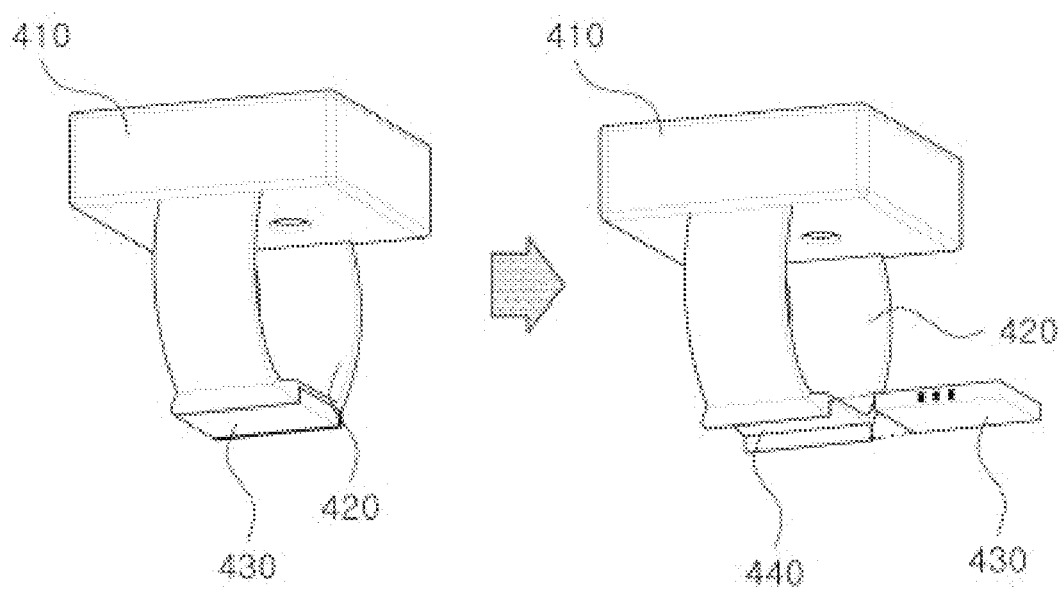
FIG. 9 is a conceptual diagram illustrating a band-type Raman signal analysis device.

FIG. 9 is a conceptual diagram illustrating a band-type continuous blood glucose measurement device.

The continuous blood glucose measurement device according to the present disclosure may be implemented in the form of a band that can be fixed to a wrist, ankle, forearm, or the like. To this end, the continuous blood glucose measurement device may include a housing 410 and a band 420.

The continuous blood glucose measurement device according to the present disclosure may further include a battery 430. The battery 430 may be disposed separately from the housing 410. For example, the battery 430 may be disposed across from the housing 410.

Further, a circuit that electrically connects components in the housing 410 to the battery 430 may be disposed within and through the band 420.

The battery 430 may be formed to be detachable from the band 420, and for this purpose, the band may include a battery coupling member 440. The battery coupling member 440 may secure the battery 430 to the band and also electrically connect the battery 430 and the circuit arranged within the band 420.

Further, an auxiliary battery may be provided within the housing 410. The auxiliary battery may ensure that the continuous blood glucose measurement device maintains its functionality without being interrupted while the battery 430 is replaced. By way of examples, the auxiliary battery may be implemented as a rechargeable battery, a coin cell, a capacitor, or the like. However, the type of auxiliary battery of the present disclosure is not limited thereto.

If the device is switched off when the battery is replaced, calibration may be necessary when restarting the blood sugar measurement after the battery replacement. This may result in an interruption in the blood sugar measurement, and the users may experience inconvenience of having to perform calibration every time the battery is replaced.

The subject matter of the present disclosure can improve user convenience by eliminating the need to turn off the device for replacing the battery.

Further, when the processor 190 causes light to be output using a plurality of light sources, it may be configured to map the light sources to correspond to each bio-information to be acquired, and may cause light to be output by differentiating the wavelength bands around the peak for extracting each bio-information.

The processor 190 may be configured to cause a light source to cycle through to extract different bio-information. The processor 190 may be configured to repeat the light output until all Raman spectra corresponding to various bio-information are acquired.

In addition, for a piece of biometric information that exceeds a preset reference range, the processor 190 may be configured to re-acquire a Raman signal using all of the plurality of light sources included in the device 100. At this time, each light source may acquire portions within the Raman spectrum range corresponding to the piece of biometric information.

Further, the disclosed embodiments may be implemented in the form of a recording medium that stores instructions executable by a computer, controller, or processor. The instructions may be stored in the form of program codes or instructions, and when executed by a processor, may generate and/or operate program modules to perform the operations of the disclosed methods according to the embodiments of the present disclosure. The recording medium may be implemented as a non-transitory computer-readable recording medium.

Computer-readable storage media may include all types of storage media capable of storing instructions that can be deciphered by a computer. Examples include Read Only Memory (ROM), Random Access Memory (RAM), magnetic tape, magnetic disk, flash memory, and optical data storage devices.

As described above, embodiments have been described with reference to the attached drawings. Those skilled in the art to which the present disclosure pertains will understand that the present disclosure can be implemented in forms other than the disclosed embodiments without departing from the technical idea or essential features of the present disclosure. The disclosed embodiments are exemplary only and should not be construed as limiting.

What is claimed is:

1. A Raman signal analysis device, comprising:
a communication unit;
a housing that forms an internal accommodation space therein;
one or more light source units that are disposed within the housing and irradiate light onto a subject;
a light receiving unit that obtains a Raman signal of light reflected or scattered from the subject using an optical filter array and an optical detection component array; and
a processor configured to analyze biological information of the subject based on the Raman signal acquired by the light receiving unit,
wherein, in response to the Raman signal analysis device being worn on a user's body, the processor is configured to control the one or more light source units and the light receiving unit to perform calibration,
wherein, when the calibration is performed, the processor is configured to:
control the one or more light source units to output the light at a predetermined intensity during a predetermined time period; and
set a light amount and an exposure time for the one or more light source units for measuring blood sugar based on a peak corresponding to a specific Raman transition value among the Raman spectrum acquired during the predetermined time period by the light receiving unit,
wherein, when the calibration is performed, the processor is configured to, in response to the Raman signal intensity corresponding to the specific Raman transition value not reaching a reference value even with the one or more light source units having reached the light amount and the exposure time, cause the communication unit to transmit an error message, and
wherein the error message includes a message requesting a change of an attachment site or re-attachment of the device.

2. The Raman signal analysis device of claim 1, wherein each of the one or more light source units comprises:
a light source that outputs light of a wavelength different from wavelengths of other light sources; and
a first lens, a first mirror, and a narrow-band optical filter disposed on a path along which the light output from the light source proceeds, and
wherein the light from the narrow-band optical filter reaches the subject through an aperture.

3. The Raman signal analysis device of claim 2, wherein the light receiving unit comprises:
a long pass filter disposed on a path of the light reflected or scattered from the subject;
an optical filter array including an optical filter that corresponds to each light of the one or more light source units;
a micro lens array that corresponds to the optical filter array; and
an optical detection component array including an optical detection component that corresponds to each of the optical filters.

4. The Raman signal analysis device of claim 1, wherein the processor is configured to extract biological information of the subject based on a peak area value of a Raman spectrum range corresponding to at least one of glucose, protein, ketone, alcohol, caffeine, lactic acid, or fat.

5. A Raman signal analysis device, comprising:
a communication unit;
a housing that forms an internal accommodation space therein;
a light source unit that is disposed within the housing and irradiates light onto a subject;
a light receiving unit that obtains a Raman signal of light reflected or scattered from the subject, wherein the light receiving unit comprises:
a beam splitter disposed on a path of the light irradiated; and
light detecting components, each of which receives the light split by the beam splitter; and
a processor configured to analyze biological information of the subject based on the Raman signal acquired by the light receiving unit,
wherein, in response to the Raman signal analysis device being worn on a user's body, the processor is configured to control the light source unit and the light receiving unit to perform calibration,
wherein, when the calibration is performed, the processor is configured to:
control the light source unit to output the light at a predetermined intensity during a predetermined time period; and
set a light amount and an exposure time for the light source unit for measuring blood sugar based on a peak corresponding to a specific Raman transition value among the Raman spectrum acquired during the predetermined time period by the light receiving unit,
wherein, when the calibration is performed, the processor is configured to, in response to the Raman signal intensity corresponding to the specific Raman transition value not reaching a reference value even with the light source unit having reached the light amount and the exposure time, cause the communication unit to transmit an error message, and
wherein the error message includes a message requesting a change of an attachment site or re-attachment of the device.

6. The Raman signal analysis device of claim 5, wherein the processor is configured to extract biological information of the subject based on a peak area value of a Raman spectrum range corresponding to at least one of glucose, protein, ketone, alcohol, caffeine, lactic acid, or fat.

7. A Raman signal analysis method performed by a Raman signal analysis device, comprising:
outputting, by one or more light source units disposed in a housing that forms an internal accommodation space therein, light of different wavelengths onto a subject;
obtaining, by a light receiving unit including an optical filter array and a light detection component array, a Raman signal of light reflected or scattered from the subject; and analyzing, by a processor, biological information of the subject based on the Raman signal acquired by the light receiving unit, wherein, in response to the Raman signal analysis device being worn on a user's body, the processor is configured to control the one or more light source units and the light receiving unit to perform calibration, wherein, when the calibration is performed, the processor is configured to:

control the one or more light source units to output the light at a predetermined intensity during a predetermined time period; and set a light amount and an exposure time for the one or more light source units for measuring blood sugar based on a peak corresponding to a specific Raman transition value among the Raman spectrum acquired during the predetermined time period by the light receiving unit, wherein, when the calibration is performed, the processor is configured to, in response to the Raman signal intensity corresponding to the specific Raman transition value not reaching a reference value even with the one or more light source units having reached the light amount and the exposure time, cause the communication unit to transmit an error message, and wherein the error message includes a message requesting a change of an attachment site or re-attachment of the device.

8. The Raman signal analysis method of claim 7, wherein each of the one or more light source units comprises:

a light source that outputs light of a wavelength different from wavelengths of other light sources; and a lens, a mirror, and a narrow-band optical filter disposed on a path along which the light output from the light source proceeds, and wherein the light from the narrow-band optical filter reaches the subject through an aperture.

9. The Raman signal analysis method of claim 8, wherein the light receiving unit comprises:

a long pass filter disposed on a path of the light reflected or scattered from the subject;

an optical filter array including an optical filter that corresponds to each light of the one or more light source units;

a micro lens array that corresponds to the optical filter array; and an optical detection component array including an optical detection component that corresponds to each of the optical filters.

\* \* \* \* \*